United States Patent
Fushimi et al.

(10) Patent No.: US 7,749,972 B2
(45) Date of Patent: Jul. 6, 2010

(54) 1-SUBSTITUTED-7-(β-D-GLYCOPYRANOSY-LOXY)(AZA)INDOLE COMPOUND AND PHARMACEUTICAL CONTAINING THE SAME

(75) Inventors: Nobuhiko Fushimi, Nagano (JP); Shigeru Yonekubo, Nagano (JP); Kohsuke Ohno, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 333 days.

(21) Appl. No.: 11/816,056

(22) PCT Filed: Feb. 14, 2006

(86) PCT No.: PCT/JP2006/302483

§ 371 (c)(1),
(2), (4) Date: Aug. 10, 2007

(87) PCT Pub. No.: WO2006/087997

PCT Pub. Date: Aug. 24, 2006

(65) Prior Publication Data

US 2009/0054356 A1    Feb. 26, 2009

(30) Foreign Application Priority Data

Feb. 15, 2005    (JP) ............................... 2005-037234

(51) Int. Cl.
*A61K 31/70*    (2006.01)
*A01N 43/04*    (2006.01)
*C07H 17/02*    (2006.01)

(52) U.S. Cl. .................... 514/35; 536/4.1; 536/17.2; 536/17.3; 536/17.4; 514/25; 514/27; 514/415; 548/469

(58) Field of Classification Search ........................ None
See application file for complete search history.

(56) References Cited

U.S. PATENT DOCUMENTS

| 2005/0032712 A1 | 2/2005 | Urbanski |
| 2005/0037981 A1 | 2/2005 | Beavers et al. |

FOREIGN PATENT DOCUMENTS

| WO | 2005/011592 A2 | 2/2005 |
| WO | WO2005/012242 | * 2/2005 |
| WO | WO2005/012243 | * 2/2005 |

OTHER PUBLICATIONS

Byrn et al., Solid-State Chemistry of Drugs, 2d, Chapter 11 Hydrates and Solvates, 233-247, 1999.*
Morissette et al., "High Throughput crystallization: polymorphs, salts, co-crystals, and solvates of pharmaceutical solids", Advanced Drug Delivery Reviews, 56 (2004) 275-300.*
Stella et al., "Prodrugs as therapeutics", Expert Opin Ther Patents, 2004, 14(3) 277-280.*
Adachi et al. "T-1095, a Renal Na+-Glucose Transporter Inhibitor, Improves Hyperglycemia in Streptozotocin-Induced Diabetic Rats", Metabolism, vol. 49 (8), Aug. 2000, pp. 990-995.*

* cited by examiner

*Primary Examiner*—Traviss C McIntosh, III
(74) *Attorney, Agent, or Firm*—Sughrue Mion, PLLC

(57) ABSTRACT

The present invention provides a compound having an SGLT1 and/or SGLT2 inhibitory activity which is usable as an agent for the prevention or treatment of diabetes, postprandial hyperglycemia, impaired glucose tolerance, diabetic complications, obesity or the like.

It is a 1-substituted-7-(β-D-glycopyranosyloxy)(aza)-indole compound represented by the general formula (I), a prodrug thereof, or a pharmaceutically acceptable salt thereof, or a hydrate or solvate thereof:

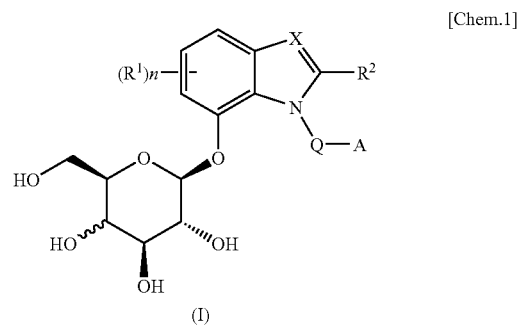

[Chem.1]

(I)

wherein $R^1$ represents a halogen atom or the like; n represents j an integer number from 0 to 3; $R^2$ represents a hydrogen atom or the like; X represents a carbon atom which a hydrogen atom or the like binds to, or a nitrogen atom; Q represents an alkylene group or an alkenylene group each of which may have an oxygen atom or a sulfur atom in the chain; and A represents an aryl or heteroaryl group which may have a substituent.

8 Claims, No Drawings

1-SUBSTITUTED-7-(β-D-GLYCOPYRANOSY-LOXY)(AZA)INDOLE COMPOUND AND PHARMACEUTICAL CONTAINING THE SAME

TECHNICAL FIELD

The present invention relates to a 1-substituted-7-(β-D-glycopyranosyloxy)(aza)indole compound. More particularly, the present invention relates to a 1-substituted-7-(β-D-glycopyranosyloxy)(aza)indole compound which can be used for the prevention or treatment of a disease associated with hyperglycemia or a disease associated with increase of galactose in blood such as diabetes, impaired glucose tolerance, diabetic complications or obesity, a prodrug thereof, a pharmaceutically acceptable salt thereof, a hydrate or solvate thereof, a pharmaceutical composition comprising the same, and a combination of the same and another pharmaceutical composition.

BACKGROUND ART

It is known that a sodium-dependent glucose transporter, hereinafter referred to as "SGLT", which is a co-transporter of monosaccharide and sodium, has some subtypes. Namely, a sodium-dependent glucose transporter 1, hereinafter referred to as "SGLT1", exists mainly in the small intestine and the S3 segment of the kidney's proximal tubule, and a sodium-dependent glucose transporter 2, hereinafter referred to as "SGLT2", exists mainly in the S1 segment of the kidney's proximal tubule.

Among them, SGLT1 which exists in the small intestine participates in glucose and galactose absorption from the digestive tract (see Non-patent references 1 and 2). In diabetic patients, carbohydrate digestion and absorption increase. Actually, it is confirmed that SGLT1 and its mRNA highly increase in the small intestine (see Non-patent reference 3). Therefore, inhibiting SGLT1 can control increase of blood sugar level by suppression of glucose and galactose absorption in the small intestine (see Patent reference 1).

On the other hand, SGLT2 participates in reabsorption of glucose filtrated through the glomerulus (see Non-patent reference 4). Therefore, inhibiting SGLT2 can normalize blood sugar level by suppression of glucose reabsorption (see Patent reference 5).

As compounds inhibiting SGLT1, pyrazole derivatives (see Patent references 1 and 2), benzylphenol derivatives (see Patent reference 3) and the like are known. And as compounds inhibiting SGLT2, glucopyranosyloxypyrazole derivatives (see Patent reference 4), glucopyranosyloxybenzylbenzene derivatives (see Patent reference 5) and the like are known.

Recently, it was reported that fused heterocyclic compounds having a glycopyranosyloxy group show an excellent SGLT inhibitory activity (see Patent reference 6). However, in the report, nothing was described or suggested concerning a compound which has a substituent on a nitrogen atom of a fused heterocyclic compound wherein the hetero atom is a nitrogen atom.

[Non-patent reference 1] Yoshikatsu Kanai, Kidney and Dialysis, 1998.12, Vol. 45, extra edition, pp. 232-237;

[Non-patent reference 2] E. Turk and 4 persons, Nature, 1991.3, Vol. 350, pp. 354-356;

[Non-patent reference 3] J. Dyer and 4 persons, American Journal of Physiology, 2002.2, Vol. 282, No. 2, pp. G241-G248;

[Non-patent reference 4] Yoshikatsu Kanai and 4 persons, J. Clin. Invest., 1994.1, Vol. 93, pp. 397-404;

[Patent reference 1] International Publication No. WO2004/014932 pamphlet;

[Patent reference 2] International Publication No. WO2004/018491 pamphlet;

[Patent reference 3] Japanese patent publication No. JP2004-196788;

[Patent reference 4] International publication No. WO01/16147 pamphlet;

[Patent reference 5] International publication No. WO01/68660 pamphlet;

[Patent reference 6] International publication No. WO2004/087727 pamphlet.

DISCLOSURE OF THE INVENTION

Objects to be Solved by the Invention

The present invention aims to provide a compound which has an SGLT1 and/or SGLT2 inhibitory activity.

Means for Solving the Problems

The present inventors have studied earnestly on compounds having an inhibitory activity against SGLT1 and/or SGLT2. As a result, it was found that certain 1-substituted-7-(β-D-glycopyranosyloxy)(aza)indole compound represented by the following general formula (I) has an excellent inhibitory activity against SGLT1 and/or SGLT2, thereby forming the basis of the present invention.

That is, the gist of the present invention resides in a 1-substituted-7-(β-D-glycopyranosyloxy)(aza)indole compound represented by the following general formula (I) or a prodrug thereof, a pharmaceutically acceptable salt thereof, or a hydrate or solvate thereof; an SGLT inhibitor comprising the same; a pharmaceutical composition comprising the same; and a combination of the same and another pharmaceutical composition.

[Chem. 1]

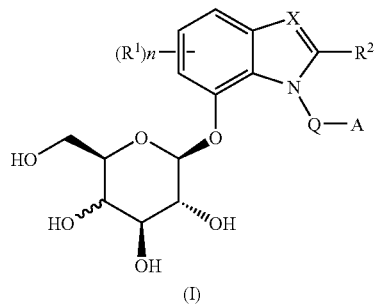

(I)

wherein $R^1$ represents a halogen atom, an alkyl group, a hydroxyalkyl group, an alkoxyalkyl group, a hydroxy group, an alkoxy group, a cycloalkyloxy group, an amino group, a (di)alkylamino group, a carboxyl group or a cyano group; n represents an integer number from 0 to 3; $R^2$ represents a hydrogen atom, a halogen atom, an alkyl group, a hydroxyalkyl group, an alkoxyalkyl group, a hydroxy group, an alkoxy group, a cycloalkyloxy group, an amino group, a (di)alkylamino group, a carboxyl group or a cyano group; X represents a carbon atom which a hydrogen atom or a group selected from a halogen atom, an alkyl group, a hydroxyalkyl group, an alkoxyalkyl group, a hydroxy group, an alkoxy group, a cycloalkyloxy group, an amino group, a (di)alkylamino group, a carboxyl group and a cyano group binds to, or a nitrogen atom; Q represents an alkylene group or an alkenylene group each of which may have an oxygen atom or a sulfur atom in the chain; and A represents an aryl or heteroaryl group which may have a substituent.

EFFECTS OF THE INVENTION

Since a 1-substituted-7-(β-D-glycopyranosyloxy)(aza)-indole compound (I) of the present invention or a prodrug thereof, a pharmaceutically acceptable salt thereof, or a hydrate or solvate thereof has an excellent inhibitory activity against SGLT1 and/or SGLT2, it can control the increase of blood sugar level, and/or lower the blood galactose level and normalize the blood sugar level.

BEST MODE TO PUT THE INVENTION TO PRACTICE

Meanings of terms used in this description are as follows.

The term "(aza)indole compound" means an indole compound which may have another nitrogen atom in the ring, and specifically, it means an indole compound or a benzimidazole compound.

The term "halogen" means fluorine, chlorine, bromine or iodine.

The term "alkyl" means optionally branched lower alkyl having 1 to 6 carbon atoms.

The term "cycloalkyl" means 3 to 7-membered cycloalkyl.

The term "alkenyl" means optionally branched lower alkenyl having 2 to 6 carbon atoms.

The term "alkynyl" means optionally branched lower alkynyl having 2 to 6 carbon atoms.

The term "alkoxy" means optionally branched lower alkoxy having 1 to 6 carbon atoms.

The term "(di)alkylamino" means monoalkylamino or dialkylamino whose two alkyls may be different.

The term "alkylene" means optionally branched lower alkylene having 1 to 6 carbon atoms.

The term "alkenylene" means optionally branched lower alkenylene having 2 to 6 carbon atoms.

The term "an alkylene group or an alkenylene group each of which may have an oxygen atom or a sulfur atom in the chain" means an alkylene group wherein an oxygen atom or a sulfur atom may exist at the end or in the center or an alkenylene group wherein an oxygen atom or a sulfur atom may exist at the end or in the center.

The term "aryl" means phenyl or naphthyl.

The term "heteroaryl" means monocyclic or fused cyclic heteroaryl having 1 or more hetero atoms selected from a group consisting of an oxygen atom, a nitrogen atom and a sulfur atom.

The term "(hetero)aryl" means aryl or heteroaryl.

The term "heterocycloalkyl" means 3 to 7-membered heterocycloalkyl having 1 or more hetero atoms selected from a group consisting of an oxygen atom, a nitrogen atom and a sulfur atom.

The term "(hetero)cycloalkyl" means cycloalkyl or heterocycloalkyl.

The term "alicyclic amine" means a heterocycloalkyl wherein the hetero atom is a nitrogen atom.

The term "acyl" means optionally branched aliphatic carboxyl acyl having 2 to 7 carbon atoms, (hetero)-cycloalkylcarboxyl acyl or (hetero)arylcarboxyl acyl.

In the general formula (I), as the glycopyranosyl group, a glucopyranosyl group or a galactopyranosyl group, especially a glucopyranosyl group, is preferable.

As $R^1$, a halogen atom, an alkyl group or a hydroxy group is preferable. When n is 2 or 3, these $R^1$ may be different.

As n, 0 is preferable.

As $R^2$, a hydrogen atom, a halogen atom, an alkyl group or a hydroxyalkyl group, especially a hydrogen atom is preferable.

As X, a carbon atom which a hydrogen atom binds to is preferable.

As Q, an alkylene group, especially an methylene group or an ethylene group is preferable.

As A, a phenyl group which may have a substituent is preferable.

As a substituent which a (hetero)aryl group may have, for example, a halogen atom, a hydroxy group and a cyano group; an alkyl group, an alkenyl group, an alkynyl group, an alkoxy group, an alkylthio group, an alkylsulfinyl group and an alkylsulfonyl group, each of which may have a substituent a (to be described below, the same hereinafter); another (hetero)aryl group and a (hetero)cycloalkyl group, each of which may have a substituent a and optionally bind to a (hetero)aryl group via an alkylene group, —O—, —NH— or —S—; a —U—V—W—N($R^4$)—Y—Z group, a —U—V—COO—Y—$R^B$ group and the like can be illustrated. Further, as a (hetero)aryl group has substituents, they may be different.

In the —U—V—W—N($R^4$)—Y—Z group or —U—V—COO—Y—$R^B$ group, U means a single bond, —O— or —S—.

V means a single bond, or an alkylene group or an alkenylene group, each of which may have a hydroxy group.

W means a single bond, —CO—, —SO$_2$— or —C(=NH)—.

$R^A$ means a hydrogen atom, or an alkyl group, a (hetero)aryl group or a (hetero)cycloalkyl group, each of which may have a substituent α.

Y means a single bond or an alkylene group which may have an oxo group.

Z means a hydrogen atom; a formyl group; or an alkyl group, a (hetero)aryl group or a (hetero)cycloalkyl group, each of which may have a substituent α; an acyl group which may have a substituent α; an alkoxy group or an arylalkoxycarbonyl group, each of which may have a substituent α; —CON($R^K$)($R^L$), —CSN($R^K$)($R^L$), —SO$_2$N($R^K$)($R^L$) or —C(=N$R^K$)N($R^L$)($R^M$); one to three amino acid residues [wherein the terminal carboxyl group is an alkoxycarbonyl group optionally having a hydroxy group, an alkoxy group, an amino group or a (di)alkylamino group; an amide with an alicyclic amine or an alkylamine, each of which may have an alkyl group, a (hetero)cycloalkyl group, an alkoxycarbonyl group or an acyl group, each of which may have a hydroxy group, an alkoxy group, an amino group or a (di)alkylamino group; or a carboxamide group]; or an aliphatic, (hetero)cycloalkyl or (hetero)aryl carboxylic acid residue having an alicyclic amine, which may have an alkyl group, a (hetero)cycloalkyl group, an alkoxycarbonyl group or an acyl group, each of which may have a hydroxy group, an alkoxy group, an amino group or a (di) alkylamino group. In addition, the term "one to three amino acid residues" means a group wherein an N terminal of an amino acid, a dipeptide or a tripeptide binds to Y, and the term "an aliphatic, (hetero)cycloalkyl or (hetero)

aryl carboxylic acid residue having an alicyclic amine" means an acyl group having an alicyclic amine (the same hereinafter).

$R^K$, $R^L$ and $R^M$ independently mean a hydrogen atom, a nitro group, a cyano group, a sulfamoyl group, an acyl group, an alkoxycarbonyl group, an aryl group, an alkylsulfonyl group or an alkyl group optionally having a substituent α.

$R^A$ and a part of a group forming Z, each of which binds to a nitrogen atom, may bind together to form an alicyclic amine optionally having a substituent α.

$R^B$ means a hydrogen atom; an alkoxyalkyl group having a carboxyl group or an alkoxycarbonyl group; an alkyl group, a (hetero)aryl group or a (hetero)cycloalkyl group, each of which may have a substituent α; one to three amino acid [wherein the terminal carboxyl group may be an alkoxycarbonyl group optionally having a hydroxy group, an alkoxy group, an amino group or a (di)alkylamino group; an amide with an alicyclic amine or an alkylamine, each of which may have an alkyl group, a (hetero)cycloalkyl group, an alkoxycarbonyl group or an acyl group, each of which may have a hydroxy group, an alkoxy group, an amino group or a (di) alkylamino group; or a carbamoyl group]; or an aliphatic, (hetero)cycloalkyl or (hetero)aryl carboxylic acid residue having an alicyclic amine, which may have an alkyl group, a (hetero)cycloalkyl group, an alkoxycarbonyl group or an acyl group, each of which may have a hydroxy group, an alkoxy group, an amino group or a (di)alkylamino group.

As the alicyclic amine, for example, pyrrolidine, piperidine, piperazine, morpholine and the like can be illustrated.

As the amino acid, for example, a natural amino acid and a synthetic amino acid may be employed. As the synthetic amino acid, a homoamino acid such as 2-methylalanine, a noramino acid such as norvaline and the like can be illustrated.

When U is —O— or —S—, V and W are not a single bond at the same time.

The substituent α means a group selected from a group consisting of a halogen atom, an alkyl group, a hydroxyalkyl group, an alkoxyalkyl group, a hydroxy group, an alkoxy group, an amino group, a (di)alkylamino group, a cyano group, a carboxyl group, a carbamoyl group, an alkoxycarbonyl group, a hydroxyalkoxycarbonyl group, a (hetero)aryl group and a (hetero)cycloalkyl group. In case that any groups have substituents, these substituents may be the same or different.

An example of the processes for preparing a 1-substituted-7-(β-D-glycopyranosyloxy)(aza)indole compound (I) of the present invention is shown below.

[Chem. 2]

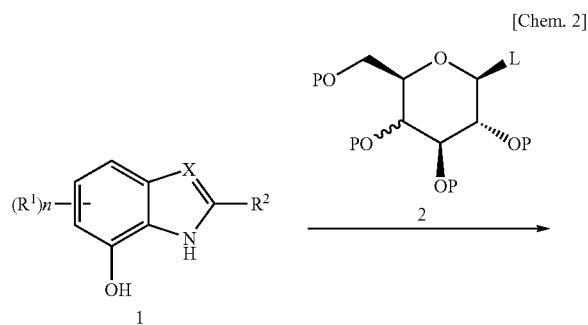

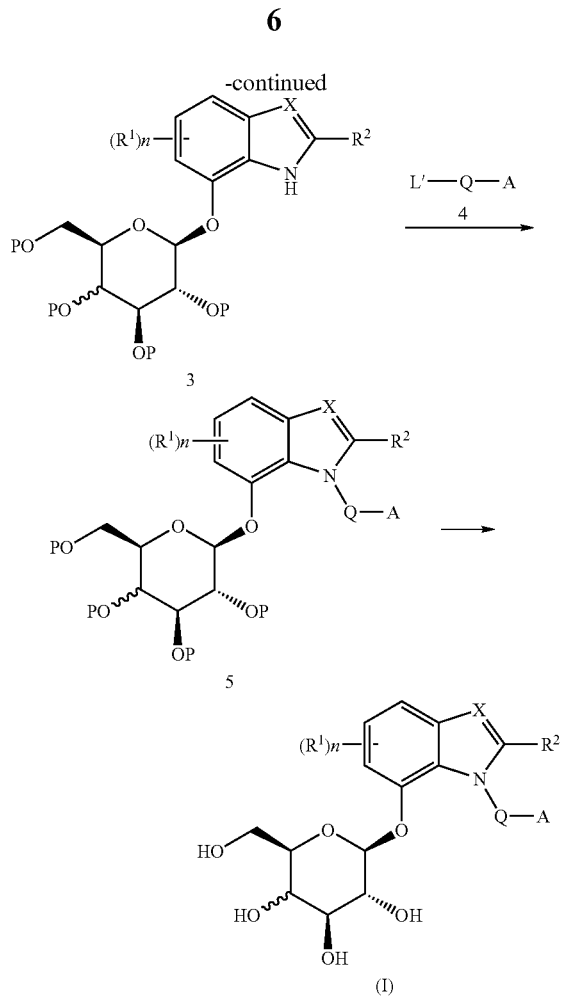

wherein $R^1$, n, $R^2$, X, Q and A have the same meanings as defined above, P represents a hydroxy-protective group, L and L' independently represent a leaving group.

A 7-hydroxy(aza)indole compound (1) is glycosylated by a hydroxy-protected D-glycopyranosyl compound (2) to obtain a 7-(β-D-glycopyranosyloxy)(aza)indole compound (3). After the compound (3) is (hetero)arylalkylated to obtain a 1-substituted-7-(β-D-glycopyranosyloxy)(aza)indole compound (5), the hydroxy-protective group can be removed to prepare a 1-substituted-7-(β-D-glycopyranosyloxy)(aza)indole compound (I).

As a hydroxy-protective group P of a D-glycopyranosyl compound (2) or a leaving group L, groups conventionally used in the field of sugar chemistry can be used. As such protective groups, for example, an acetyl group, a pivaloyl group and the like can be illustrated. As leaving groups, for example, a bromine atom, a trichloroacetimidoyloxy group and the like can be illustrated.

As a leaving group L' of a (hetero)arylalkylating reagent (4), for example, a chlorine atom, a bromine atom, a mesyloxy group and tosyloxy group and the like can be illustrated.

In case that the leaving group L is a bromine atom, it is preferable that glycosilation is conducted in the presence of a base such as sodium carbonate, potassium carbonate, cesium carbonate, sodium hydroxide, potassium hydroxide, sodium hydride or the like, and more preferable that a phase-transfer catalyst such as benzyltributylammonium chloride, benzyltributylammonium bromide, tetrabutylammonium hydrogen sulfate or the like is also added. In addition, in case that the leaving group L is trichloroacetimidoyloxy group, it is preferable that glycosilation is conducted in the presence of a Lewis acid such as boron trifluoride diethyl ether complex, trimethylsilyl trifluoromethanesulfonate, tin tetrachloride or the like.

The (hetero)arylalkylation is preferably conducted in the presence of a base such as sodium hydride, potassium carbonate, cesium carbonate, potassium t-butoxide or the like. If desired, sodium iodide can be added.

In case that an acetyl group or a pivaloyl group is used as a hydroxy-protective group, these groups can be removed by general alkaline hydrolysis using sodium hydroxide, lithium hydroxide, sodium methoxide, sodium ethoxide or the like.

A 1-substituted-7-(β-D-glycopyranosyloxy)(aza)indole compound (I) can be also prepared through each process of the above (hetero)arylalkylation, glycosilation and deprotection after protecting a hydroxy group at 7-position of a 7-hydroxy(aza)indole compound (1) by a (substituted) benzyl group such as a benzyl group, a benzhydryl group or the like. In addition, the (substituted) benzyl group can be removed according to conventional methods such as hydrogenolysis or hydrolysis.

A 7-hydroxy(aza)indole compound (1) or a compound hydroxy-protected by a benzyl group or the like at the 7-position thereof is commercially available or can be prepared according to known methods, for example, Synthetic Communications, Vol. 21, No. 5, pp. 611-617, 1991; synthetic Communications, Vol. 33, No. 3, pp. 507-514, 2003; Heterocycles, Vol. 38, No. 11, pp. 2415-2442, 1994; Tetrahedron Letters, Vol. 46, pp. 1021-1022, 2005 and the like.

In addition, a 7-(β-D-glycopyranosyloxy(aza)indole compound (3) wherein X is a nitrogen atom and $R^2$ is a hydrogen atom, that is, a 7-(β-D-glycopyranosyloxy)benzimidazole compound (3') can be prepared by the method described below.

[Chem. 3]

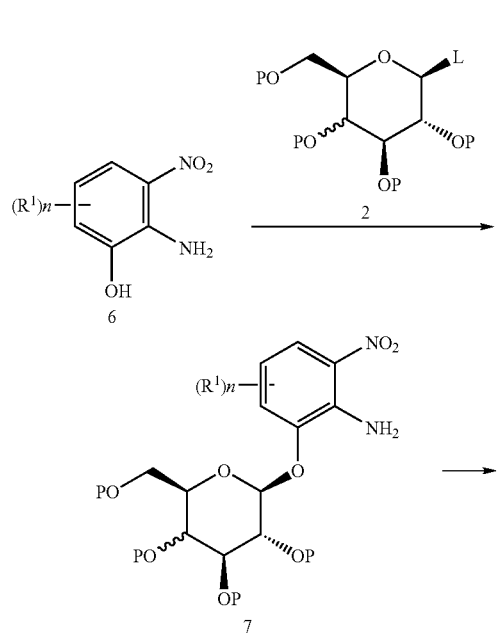

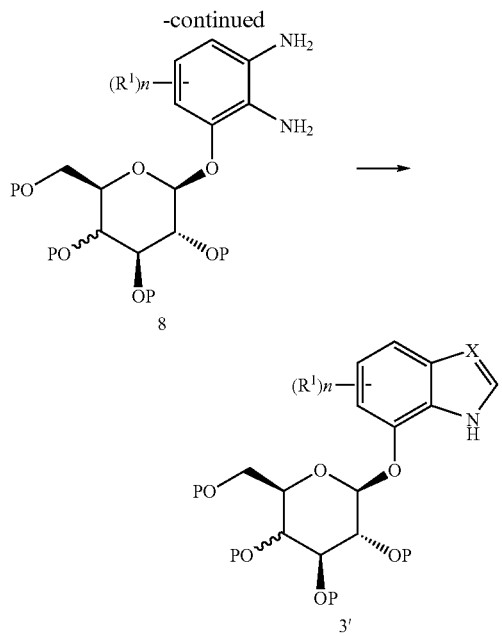

wherein $R^1$, n, L and P have the same meanings as defined above.

That is, a 2-amino-3-nitrophenol compound (6) is glycosylated to obtain an o-nitroaniline glycosylated compound (7). An o-phenylenediamine glycosylated compound (8) is prepared by reducing the nitro group thereof. A 7-(β-D-glycopyranosyloxy)benzimidazole compound (3') can be prepared by subjecting the o-phenylenediamine glycosylated compound (8) to react with orthoformate ester such as trimethyl orthoformate to cyclize.

An agent for (hetero)arylalkylation (4) is commercially available or can be prepared from an easily available (hetero) aryl compound by optionally combining conventional reactions such as halogenation, amination, nitration, sulfonation, diazotization, thiolation, esterification, amidation, oxidation, reduction, dehydrative condensation, hydrolization, coupling and the like (for example, see WO2004/014932 and WO2004/018491 pamphlets). In addition, when a compound used or generated in the above-mentioned preparation methods has a functional group which changes under the reaction condition or inhibits the reaction progression, the group may be protected by an appropriate protective group commonly used by a skilled person in the art and the protective group may be removed in an appropriate step.

A 1-substituted-7-(β-D-glycopyranosyloxy)(aza)indole compound represented by the general formula (I) of the present invention can be converted into a prodrug wherein the carboxyl group, hydroxy group and/or amino group is converted, by allowing to react with a reagent to produce a prodrug such as a halogenated alkyl such as ethyl chloride, benzyl chloride or the like; a halogenated acyl such as acetyl chloride, benzoyl chloride or the like; a halogenated formate ester such as ethyl chloroformate ester, benzyl chloroformate ester or the like.

A 1-substituted-7-(β-D-glycopyranosyloxy)(aza)indole compound represented by the general formula (I) or a prodrug thereof can be derived into a pharmaceutically acceptable salt thereof in the usual way. As such a salt, for example, a salt with an inorganic acid such as hydrochloric acid, nitric acid or the like; a salt with an organic acid such as acetic acid, methanesulfonic acid or the like; and a sodium salt and potassium salt; an additive salt with an organic base such as N,N'-dibenzylethylenediamine, 2-aminoethanol or the like can be illustrated.

A 1-substituted-7-(β-D-glycopyranosyloxy)(aza)indole compounds represented by the general formula (I) or a prodrug thereof sometimes can be obtained as a hydrate or solvate in the course of purification or preparing salts thereof. For a pharmaceutical composition of the present invention, either of a 1-substituted-7-(β-D-glycopyranosyloxy)(aza)indole compound or a prodrug thereof, or a pharmaceutically acceptable salt thereof, or a hydrate or solvate thereof can be used.

Furthermore, a 1-substituted-7-(β-D-glycopyranosyl-oxy)(aza)indole compound represented by the general formula (I) or a prodrug thereof sometimes has tautomers, geometrical isomers and/or optical isomers. For the pharmaceutical composition of the present invention, any of the isomers and a mixture thereof can be employed.

A Pharmaceutical composition of the present invention may be prepared by mixing a 1-substituted-7-(β-D-glycopyranosyloxy)(aza)indole compound (I) or a prodrug thereof, or a pharmaceutically acceptable salt thereof, or a hydrate or solvate thereof and a conventional pharmaceutical carrier.

The pharmaceutical carrier may be used optionally in combination according to a dosage form as described below. As the pharmaceutical carrier, additives such as lactose or the like; lubricants such as magnesium stearate or the like; disintegrators such as carboxymethyl cellulose or the like; binders such as hydroxypropylmethylcellulose or the like; surfactants such as macrogol or the like; foamings such as sodium bicarbonate or the like; dissolving aids such as cyclodextrin or the like; acidities such as citric acid or the like; stabilizers such as sodium edeate or the like; pH controls such as phosphoric acid salt or the like can be illustrated.

As the dosage form of the pharmaceutical composition of the present invention, oral administrations such as powders, granules, fine granules, dry syrups, tablets, capsules and the like; parenteral administrations such as injections, poultices, suppositories and the like are illustrated.

As the 1-substituted-7-(β-D-glycopyranosyloxy)(aza)-indole compound represented by the general formula (I) shows a potent inhibitory activity against human SGLT1 and/or SGLT2 in human SGLT1 and SGLT2 inhibitory activity confirmatory tests, it can inhibit the postprandial increase of the blood sugar level increase by inhibiting the absorption of glucose or galactose, and/or normalize the blood glucose level by lowering the blood galactose level or inhibiting the reabsorption of glucose. Accordingly, the pharmaceutical composition of the present invention can be used as an inhibitor of postprandial hyperglycemia, or as an agent for the prevention or treatment of a disease selected from a group consisting of diabetes, impaired glucose tolerance, diabetic complications (for example, retinopathy, neuropathy, nephropathy, ulcer, macroangiopathy), obesity, hyperinsulinemia, galactosemia, hyperlipidemia, hypercholesterolemia, hypertriglyceridemia, lipid metabolism disorder, atherosclerosis, hypertension, metabolic syndrome, congestive heart failure, edema, hyperuricemia and gout, or the inhibition of impaired glucose tolerance advancing into diabetes.

For manufacturing the above agent for the prevention or treatment, the dosage of the 1-substituted-7-(β-D-glycopyranosyloxy)(aza)indole compound represented by the general formula (I) of the present invention or a pharmaceutically acceptable salt thereof, or a hydrate or solvate thereof is appropriately within the range of from 0.1 to 1,000 mg per day per adult human in case of oral administration and approximately within the range of from 0.01 to 100 mg per day per adult human in the case of parenteral injection in the formulation.

Furthermore, a drug of the present invention can be used in combination with other drug(s). Examples of such other drugs include an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, an 11β-hydroxysteroiddehydrogenaze inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhidantoin, EGB-761, bimoclomol, sulodexide, Y-128, an antidiarrhoics, a cathartics, a hydroxymethylglutaryl coenzyme A reductase inhibitor, a fibrate, a β₃-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a squalene epoxidase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α₂-adrenoceptor agonist, an antiplatelets agent, a uric acid synthesis inhibitor, a uricosuric agent, and a urinary alkalinizer.

As an insulin sensitivity enhancer, for example, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-αγ agonists such as GW-409544, KRP-297, N,N-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, N,N-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for the prevention or treatment of diabetes, impaired glucose tolerance, diabetic complications, obesity, hyperinsulinemia, hyperlipidemia, hypercholesterolemia, hypertriglyceridemia, lipid metabolism disorder or atherosclerosis, and more preferably for the prevention or treatment of diabetes, impaired glucose tolerance or hyperinsulinemia because of improving the disturbance of insulin signal transduction in peripheral tissues and enhancing glucose uptake into the tissues from the blood, leading to lowering of blood glucose level.

As an amylase inhibitor, for example, RSH-2083 and the like are illustrated.

As an α-glucosidase inhibitor, for example, α-glucosidase inhibitors such as acarbose, voglibose, miglitol, CKD-711, emiglitate, MDL-25, 637, camiglibose and MDL-73, 945, AZM-127 and the like are illustrated.

Amylase inhibitors and α-glucosidase inhibitors are used preferably for the prevention or treatment of diabetes, impaired glucose tolerance, diabetic complications, obesity or hyperinsulinemia, and more preferably for the prevention or treatment of impaired glucose tolerance because of inhibiting the gastrointestinal enzymatic digestion of carbohydrates contained in foods, and inhibiting or delaying the absorption of glucose or the like into the body.

As a biguanide, for example, phenformin, buformin hydrochloride, metformin hydrochloride and the like are illustrated. Biguanides are used preferably for the prevention or treatment of diabetes, impaired glucose tolerance, diabetic complications or hyperinsulinemia, and more preferably for the prevention or treatment of diabetes, impaired glucose tolerance or hyperinsulinemia because of lowering blood glucose level by inhibitory effects on hepatic gluconeogenesis, accelerating effects on anaerobic glycolysis in tissues or improving effects on insulin resistance in peripheral tissues.

As an insulin secretion enhancer, for example, tolbutamide, chlorpropamide, tolazamide, acetohexamide, glyclopyramide, glyburide (glibenclamide), gliclazide, 1-butyl-3-metanilyl-urea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide and the like are illustrated. In addition, the insulin secretion enhancers include glucokinase activators such as RO-28-1675. Insulin secretion enhancers are used preferably for the prevention or treatment of diabetes, impaired glucose tolerance or diabetic complications, and more preferably for the prevention or treatment of diabetes or impaired glucose tolerance because of lowering blood glucose level by acting on pancreatic β-cells and enhancing the insulin secretion.

As insulin or an insulin analogue, for example, human insulin, animal-derived insulin, human or animal-derived insulin analogues and the like are illustrated. These preparations are used preferably for the prevention or treatment of diabetes, impaired glucose tolerance or diabetic complications, and more preferably for the prevention or treatment of diabetes or impaired glucose tolerance.

As a glucagon receptor antagonist, for example, BAY-27-9955, NNC-92-1687 and the like are illustrated; as insulin receptor kinase stimulants, TER-17411, L-783281, KRX-613 and the like are illustrated; as tripeptidyl peptidase II inhibitors, UCL-1397 and the like are illustrated; as dipeptidyl peptidase IV inhibitors, for example, NVP-DPP2728A, TSL-225, P-32/98, MK-0431 and the like are illustrated; as protein tyrosine phosphatase 1B inhibitors, for example, PTP-112, OC-86839, PNU-177496 and the like are illustrated; as glycogen phosphorylase inhibitors, for example, N,N-4201, inglifolib and the like are illustrated; as fructose-bisphosphatase inhibitors, for example, CS-917 and the like are illustrated; as pyruvate dehydrogenase inhibitors, for example, AZD-7545 and the like are illustrated; as hepatic gluconeogenesis inhibitors, for example, FR-225659 and the like are illustrated; as an 11β-hydroxysteroid-dehydrogenaze inhibitor, for example, BVT-3498, HM-2002 and the like are illustrated; as glucagon-like peptide-1 analogues, for example, exendin-4, CJC-1131 and the like are illustrated; as glucagon-like peptide 1 agonists; AZM-134, LY-315902 and the like are illustrated; and as amylin, amylin analogues or amylin agonists, for example, pramlintide acetate and the like are illustrated. These drugs, glucose-6-phosphatase inhibitors, D-chiroinositol, glycogen synthase kinase-3 inhibitors and glucagon-like peptide-1 are used preferably for the prevention or treatment of diabetes, impaired glucose tolerance, diabetic complications or hyperinsulinemia, and more preferably for the prevention or treatment of diabetes or impaired glucose tolerance.

As an aldose reductase inhibitor, for example, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat and the like are illustrated. Aldose reductase inhibitors are used preferably for the prevention or treatment of diabetic complications because of inhibiting aldose reductase and lowering excessive intracellular accumulation of sorbitol in accelerated polyol pathway which are in continuous hyperglycemic condition in the tissues in diabetic complications.

As an advanced glycation endproduct formation inhibitors, for example, pyridoxamine, OPB-9195, ALT-946, ALT-711, pimagedine hydrochloride and the like are illustrated. Advanced glycation endproducts formation inhibitors are used preferably for the prevention or treatment of diabetic complications because of inhibiting formation of advanced glycation endproducts which are accelerated in continuous hyperglycemic condition in diabetes and declining of cellular damage.

As a protein kinase C inhibitor, for example, LY-333531, midostaurin and the like are illustrated. Protein kinase C inhibitors are used preferably for the prevention or treatment of diabetic complications because of inhibiting of protein kinase C activity which is accelerated in continuous hyperglycemic condition in diabetes.

As a γ-aminobutyric acid receptor antagonist, for example, topiramate and the like are illustrated; as sodium channel antagonists, for example, mexiletine hydrochloride, oxcarbazepine and the like are illustrated; as transcrit factor NF-κB inhibitors, for example, dexlipotam and the like are illustrated; as lipid peroxidase inhibitors, for example, tirilazad mesylate and the like are illustrated; as N-acetylated-α-linked-acid-dipeptidase inhibitors, for example, GPI-5693 and the like are illustrated; and as carnitine derivatives, for example, carnitine, levacecamine hydrochloride, levocarnitine chloride, levocarnitine, ST-261 and the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are used preferably for the prevention or treatment of diabetic complications.

As an antidiarrhoics or cathartic, for example, polycarbophil calcium, albumin tannate, bismuth subnitrate and the like are illustrated. These drugs are used preferably for the prevention or treatment of diarrhea, constipation or the like accompanying diabetes or the like.

As a hydroxymethylglutaryl coenzyme A reductase inhibitor, for example, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin and the like are illustrated. Hydroxymethylglutaryl coenzyme A reductase inhibitors are used preferably for the prevention or treatment of hyperlipidemia, hypercholesterolemia, hypertriglyceridemia, lipid metabolism disorder or atherosclerosis, and more preferably for the prevention or treatment of hyperlipidemia, hypercholesterolemia or atherosclerosis because of lowering blood cholesterol level by inhibiting hydroxymethylglutaryl coenzyme A reductase.

As a fibrate, for example, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 and the like are illustrated. Fibric acid derivatives are used preferably for the prevention or treatment of hyperinsulinemia, hyperlipidemia, hypercholesterolemia, hypertriglyceridemia, lipid metabolism disorder or atherosclerosis, and more preferably for the prevention or treatment of hyperlipidemia, hypertriglyceridemia or atherosclerosis because of activating hepatic lipoprotein lipase and enhancing fatty acid oxidation, leading to lowering of blood triglyceride level.

As a $\beta_3$-adrenoceptor agonist, for example, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, YM178, KTO-7924 and the like are illustrated. $\beta_3$-Adrenoceptor agonists are used preferably for the prevention or treatment of obesity, hyperinsulinemia, hyperlipidemia, hypercholesterolemia, hypertriglyceridemia or lipid metabolism disorder, and more preferably for the prevention or treatment of obesity or hyperinsulinemia because of stimulating $\beta_3$-adrenoceptor in adipose tissue and enhancing the fatty acid oxidation, leading to induction of energy expenditure.

As an acyl-coenzyme A cholesterol acyltransferase inhibitor, for example, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe and the like are illustrated. Acyl-coenzyme A cholesterol acyltransferase inhibitors are used preferably for the prevention or treatment of hyperlipidemia, hypercholesterolemia, hypertriglyceridemia or lipid metabolism disorder, and more preferably for the prevention or treatment of hyperlipidemia or hypercholesterolemia because of lowering blood cholesterol level by inhibiting acyl-coenzyme A cholesterol acyltransferase.

As a thyroid hormone receptor agonist, for example, sodium liothyronine, sodium levothyroxine, KB-2611 and the like are illustrated; as cholesterol absorption inhibitor, for example, ezetimibe, SCH-48461 and the like are illustrated; as lipase inhibitor, for example, orlistat, ATL-962, AZM-131, RED-103004 and the like are illustrated; as carnitine palmitoyltransferase inhibitor, for example, etomoxir and the like are illustrated; as squalene synthase inhibitor, for example, SDZ-268-198, BMS-188494, A-87049, RPR-101821, ZD-9720, RPR-107393, ER-27856, TAK-475 and the like are illustrated; as nicotinic acid derivative, for example, nicotinic acid, nicotinamide, nicomol, niceritrol, acipimox, nicorandil and the like are illustrated; as bile acid sequestrant, for example, colestyramine, colestilan, colesevelam hydrochloride, GT-102-279 and the like are illustrated; as sodium/bile acid cotransporter inhibitor, for example, 264W94, S-8921, SD-5613 and the like are illustrated; and as cholesterol ester transfer protein inhibitor, for example, PNU-107368E, SC-795, JTT-705, CP-529414 and the like are illustrated. These drugs, probcol, microsomal triglyceride transfer protein inhibitor, lipoxygenase inhibitor, squalene epoxidase inhibitor and low-density lipoprotein receptor enhancer are used preferably for the prevention or treatment of hyperlipidemia, hypercholesterolemia, hypertriglyceridemia or lipid metabolism disorder.

As an appetite suppressant, for example, monoamine reuptake inhibitor, serotonin reuptake inhibitor, serotonin releasing stimulant, serotonin agonist (especially $5HT_{2C}$-agonist), noradrenaline reuptake inhibitor, noradrenaline releasing stimulant, $\alpha_1$-adrenoceptor agonist, $\beta_2$-adrenoceptor agonist, dopamine agonist, cannabinoid receptor antagonist, $\gamma$-aminobutyric acid receptor antagonist, $H_3$-histamine antagonist, L-histidine, leptin, leptin analogue, leptin receptor agonist, melanocortin receptor agonist (especially, MC3-R agonists, MC4-R agonist), $\alpha$-melanocyte stimulating hormone, cocaine- and amphetamine-regulated transcript, mahogany protein, enterostatin agonist, calcitonin, calcitonin-gene-related peptide, bombesin, cholecystokinin agonist (especially CCK-A agonist), corticotropin-releasing hormone, corticotropin-releasing hormone analogue, corticotropin-releasing hormone agonist, urocortin, somatostatin, somatostatin analogues, somatostatin receptor agonist, pituitary adenylate cyclase-activating peptide, brain-derived neurotrophic factor, ciliary neurotrophic factor, thyrotropin-releasing hormone, neurotensin, sauvagine, neuropeptide Y antagonists, PYY, opioid peptide antagonist, galanin antagonist, melanin-concentrating hormone receptor antagonist, agouti-related protein inhibitor and orexin receptor antagonist are illustrated. Concretely, as monoamine reuptake inhibitor, mazindol and the like are illustrated; as serotonin reuptake inhibitor, dexfenfluramine hydrochloride, fenfluramine, sibutramine hydrochloride, fluvoxamine maleate, sertraline hydrochloride and the like are illustrated; as serotonin agonist, inotriptan, (+)-norfenfluramine and the like are illustrated; as noradrenaline reuptake inhibitor, bupropion, GW-320659 and the like are illustrated; as noradrenaline releasing stimulant, rolipram, YM-992 and the like are illustrated; as $\beta_2$-adrenoceptor agonist, amphetamine, dextroamphetamine, phentermine, benzphetamine, methamphetamine, phendimetrazine, phenmetrazine, diethylpropion, phenylpropanolamine, clobenzorex and the like are illustrated; as dopamine agonist, ER-230, doprexin, bromocriptine mesylate and the like are illustrated; as cannabinoid receptor antagonist, rimonabant and the like are illustrated; as $\gamma$-aminobutyric acid receptor antagonist, topiramate and the like are illustrated; as $H_3$-histamine antagonist, GT-2394 and the like are illustrated; as leptin, leptin analogues or leptin receptor agonist, LY-355101 and the like are illustrated; as cholecystokinin agonist (especially CCK-A agonist), SR-146131, SSR-125180, BP-3.200, A-71623, FPL-15849, GI-248573, GW-7178, GI-181771, GW-7854, A-71378 and the like are illustrated; and as neuropeptide Y antagonist, SR-120819-A, PD-160170, NGD-95-1, BIBP-3226, 1229-U-91, CGP-71683, BIBO-3304, CP-671906-01, J-115814 and the like are illustrated. Appetite suppressant are used preferably for the prevention or treatment of diabetes, impaired glucose tolerance, diabetic complications, obesity, hyperlipidemia, hyper-cholesterolemia, hypertriglyceridemia, lipid metabolism disorder, atherosclerosis, hypertension, congestive heart failure, edema, hyperuricemia or gout, and more preferably for the prevention or treatment of obesity because of stimulating or inhibiting the activities of intracerebral monoamines or bioactive peptides in central appetite regulatory system and suppressing the appetite, leading to reduction of energy intake.

As an angiotensin-converting enzyme inhibitor, for example, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril and the like are illustrated. Angiotensin-converting enzyme inhibitors are used preferably for the prevention or treatment of diabetic complications or hypertension.

As a neutral endopeptidase inhibitor, for example, omapatrilat, MDL-100240, fasidotril, sampatrilat, GW-660511X, mixanpril, SA-7060, E-4030, SLV-306, ecadotril and the like are illustrated. Neutral endopeptidase inhibitors are used preferably for the prevention or treatment of diabetic complications or hypertension.

As an angiotensin II receptor antagonist, for example, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 and the like are illustrated. Angiotensin II receptor antagonists are used preferably for the prevention or treatment of diabetic complications or hypertension.

As an endothelin-converting enzyme inhibitor, for example, CGS-31447, CGS-35066, SM-19712 and the like are illustrated; as endothelin receptor antagonists, for example, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 and the like are illustrated. These drugs are used preferably for the prevention or treatment of diabetic complications or hypertension, and more preferably for the prevention or treatment of hypertension.

As a diuretic agent, for example, chlorthalidone, metolazone, cyclopenthiazide, trichloromethiazide, hydrochlorothiazide, hydroflumethiazide, benzylhydrochloro-thiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride and the like are illustrated. Diuretic drugs are used preferably for the prevention or treatment of diabetic complications, hypertension, congestive heart failure or edema, and more preferably for the prevention or treatment of hypertension, congestive heart failure or edema because of reducing blood pressure or improving edema by increasing urinary excretion.

As a calcium antagonist, for example, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride and the like are illustrated; as vasodilating antihypertensive agents, for example, indapamide, todralazine hydrochloride, hydralazine hydrochloride, cadralazine, budralazine and the like are illustrated; as sympathetic blocking agents, for example, amosulalol hydrochloride, terazosin hydrochloride, bunazosinhydrochloride, prazosinhydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin and the like are illustrated; as centrally acting antihypertensive agent, for example, reserpine and the like are illustrated; and as $\alpha_2$-adrenoceptor agonist, for example, clonidine hydrochloride, methyldopa, CHF-1035, guanabenz acetate, guanfacine hydrochloride, moxonidine, lofexidine, talipexole hydrochloride and the like are illustrated. These drugs are used preferably for the prevention or treatment of hypertension.

As an antiplatelets agent, for example, ticlopidine hydrochloride, dipyridamole, cilostazol, ethyl icosapentate, sarpogrelate hydrochloride, dilazep dihydrochloride, trapidil, beraprost sodium, aspirin and the like are illustrated. Antiplatelets agents are used preferably for the prevention or treatment of atherosclerosis or congestive heart failure.

As a uric acid synthesis inhibitor, for example, allopurinol, oxypurinol, febuxostat and the like are illustrated; as uricosuric agents, benzbromarone, probenecid and the like are illustrated; and as urinary alkalinizers, sodium hydrogen carbonate, potassium citrate, sodium citrate and the like are illustrated. These drugs are used preferably for the prevention or treatment of hyperuricemia or gout.

As the other drug combined with the 1-substituted-7-(β-D-glycopyranosyloxy)(aza)indole compound of the present invention in the use for the prevention or treatment of diabetes, for example, the drug selected from at least one member of the group consisting of an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, an 11β-hydroxysteroiddehydrogenase inhibitor, glucagon-like peptide-1, a glucagon-like peptide-1 analogue, a glucagon-like peptide-1 agonist, amylin, an amylin analogue, an amylin agonist and an appetite suppressant is preferable; the drug selected from at least one member of the group consisting of an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, an 11β-hydroxysteroid-dehydrogenase inhibitor, glucagon-like peptide-1, a glucagon-like peptide-1 analogue, a glucagon-like peptide-1 agonist, amylin, an amylin analogue and an amylin agonist is more preferable; and the drug selected from at least one member of the group consisting of an insulin sensitivity enhancer, an amylase inhibitor, an α-glucosidase inhibitor, a biguanide, an insulin secretion enhancer and an insulin or insulin analogue is most preferable.

In the use for the prevention or treatment of diabetic complications, for example, the drug selected from at least one member of the group consisting of an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, glycogen synthase kinase-3 inhibitors, an 11β-hydroxysteroiddehydrogenase inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhidantoin, EGB-761, bimoclomol, sulodexide, Y-128, an antidiarrhoics, a cathartics, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the drug selected from at least one member of the group consisting of an aldose reductase inhibitor, an angiotensin-converting enzyme inhibitor, a neutral endopeptidase inhibitor and an angiotensin II receptor antagonist is more preferable.

In the use for the prevention or treatment of obesity, the drug selected from at least one member of the group consisting of an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, an 11β-hydroxysteroiddehydrogenase inhibitor, glucagon-like peptide-1, a glucagon-like peptide-1 analogue, a glucagon-like peptide-1 agonist, amylin, an amylin analogue, an amylin agonist, a β$_3$-adrenoceptor agonist and an appetite suppressant is preferable; and the drug selected from at least one member of the group consisting of an amylase inhibitor, an α-glucosidase inhibitor, a β$_3$-adrenoceptor agonist and an appetite suppressant is more preferable.

EXAMPLES

The present invention is further illustrated in more detail by way of the following Reference Examples, Examples and Test Examples. However, the present invention is not limited thereto.

Reference Example 1

7-Hydroxy-1-(4-methylbenzyl)-1H-indole

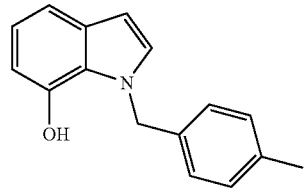

[Chem. 4]

To a solution of 7-benzyloxy-1H-indole (0.3 g) in N,N-dimethylformamide (5 mL) was added sodium hydride (55% 70 mg) under ice-cooling, and the mixture was stirred for 10 minutes. To the reaction mixture was added 4-methylbenzyl chloride (0.19 mL), and the mixture was stirred at room temperature for 2 hours. The reaction mixture was poured into water, and the resulting mixture was extracted with diethyl ether. The extract was washed with water and brine, and dried over anhydrous magnesium sulfate. The solvent was removed under reduced pressure to give 7-benzyloxy-1-(4-methylbenzyl)-1H-indole (0.43 g). This material was dissolved in tetrahydrofuran (6 mL). To the solution was added 10% palladium-carbon powder (50 mg), and the mixture was stirred at room temperature under a hydrogen atmosphere for 5 hours. The insoluble material was removed by filtration, and the filtrate was concentrated under reduced pressure. The residue was purified by column chromatography on silica gel (eluent: n-hexane/ethyl acetate=5/1) to give the title compound (86 mg).

$^1$H-NMR (CDCl$_3$) δ ppm:

2.3 (3H, s), 4.68 (1H, s), 5.6 (2H, s), 6.45-6.5 (2H, m), 6.89 (1H, t, J=7.7 Hz), 7.0-7.1 (5H, m), 7.15-7.25 (1H, m).

Reference Example 2

7-Hydroxy-1-{2-[4-(3,3-dimethoxypropoxy)phenyl]ethyl}-1H-indole

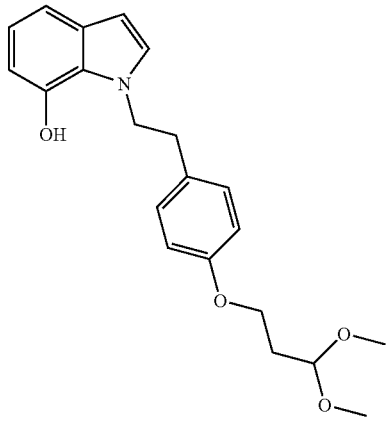

[Chem. 5]

A mixture of 4-(2-hydroxyethyl)phenol (1 g), 3-bromopropionaldehyde dimethyl acetal (1.02 mL), cesium carbonate (2.83 g) and a catalytic amount of sodium iodide in acetone (15 mL) was stirred at room temperature overnight. The insoluble material was removed by filtration, and the filtrate was concentrated under reduced pressure. The residue was purified by column chromatography on aminopropylated silica gel (eluent: n-hexane/ethyl acetate=1/1) to give 3-[4-(2-hydroxy-ethyl)phenyloxy]propionaldehyde dimethyl acetal (1.22 g). This material was dissolved in methylene chloride (15 mL). To the solution were added triethylamine (0.85 mL) and methanesulfonyl chloride (0.43 mL) under ice-cooling, and the mixture was stirred for 1 hour. The reaction mixture was poured into water, and the resulting mixture was extracted with ethyl acetate. The ethyl acetate solution was washed with 0.5 mol/L hydrochloric acid, water and brine successively, and dried over anhydrous magnesium sulfate. The solvent was removed under reduced pressure to give 3-[4-(2-methanesulfonyloxyethyl)-phenyloxy]propionaldehyde dimethyl acetal (1.49 g). To a solution of 7-benzyloxy-1H-indole (1.04 g) in N,N-dimethyl-formamide (10 mL) was added sodium hydride (55% 0.25 g) under ice-cooling, and the mixture was stirred for 10 minutes. To the reaction mixture were added the above 3-[4-(2-methane-sulfonyloxyethyl)phenyloxy]propionaldehyde dimethyl acetal (1.49 g) and a catalytic amount of sodium iodide, and the mixture was stirred at room temperature overnight. The reaction mixture was poured into water, and the resulting mixture was extracted with diethyl ether. The extract was washed with water and brine, and dried over anhydrous magnesium sulfate. The solvent was removed under reduced pressure, and the residue was purified by column chromatography on silica gel (eluent: n-hexane/ethyl acetate=6/1-5/1) to give 7-benzyloxy-1-{2-[4-(3,3-dimethoxypropoxy)phenyl]ethyl}-1H-indole. This material was dissolved in tetrahydrofuran (10 mL). To the solution was added 10% palladium-carbon powder (0.5 g), and the mixture was stirred at room temperature under a hydrogen atmosphere for 5 hours. The insoluble material was removed by filtration, and the filtrate was concentrated under reduced pressure to give the title compound (1.57 g).

$^1$H-NMR (CDCl$_3$) δ ppm:
2.05-2.1 (2H, m), 3.0-3.1 (2H, m), 3.37 (6H, s), 4.01 (2H, t, J=6.2 Hz), 4.5-4.6 (2H, m), 4.63 (1H, t, J=5.9 Hz), 4.86 (1H, brs), 6.36 (1H, d, J=3.3 Hz), 6.5 (1H, d, J=7.4 Hz), 6.75-6.85 (3H, m), 6.89 (1H, t, J=7.4 Hz), 6.95-7.05 (2H, m), 7.15-7.25 (1H, m).

Reference Examples 3 to 6

The compounds described in Table 1 were prepared in a similar manner to that described in Reference Example 1 or Reference Example 2 using the corresponding starting materials.

TABLE 1

| No. | Structure Formula | $^1$H-NMR (CDCl$_3$) δ ppm: |
|---|---|---|
| Reference Example 3 | | 3.76 (3H, s), 4.77 (1H, brs), 5.57 (2H, s), 6.45-6.5 (2H, m), 6.75-6.85 (2H, m), 6.89 (1H, t, J = 7.9 Hz), 7.04 (1H, d, J = 3.3 Hz), 7.05-7.15 (2H, m), 7.15-7.25 (1H, m). |
| Reference Example 4 | | 1.7 (1H, t, J = 5.3 Hz), 1.95-2.05 (2H, m), 3.8-3.9 (2H, m), 4.07 (2H, t, J = 5.9 Hz), 4.84 (1H, brs), 5.57 (2H, s), 6.45-6.5 (2H, m), 6.75-6.85 (2H, m), 6.89 (1H, t, J = 7.7 Hz), 7.03 (1H, d, J = 3.0 Hz), 7.05-7.1 (2H, m), 7.15-7.25 (1H, m). |

TABLE 1-continued

| No. | Structure Formula | ¹H-NMR (CDCl₃) δ ppm: |
|---|---|---|
| Reference Example 5 | 7-hydroxy-1-(2-phenylethyl)-1H-indole | 3.1-3.2 (2H, m), 4.55-4.65 (2H, m), 4.88 (1H, s), 6.37 (1H, d, J = 3.0 Hz), 6.51 (1H, d, J = 7.6 Hz), 6.7-6.8 (1H, m), 6.83 (1H, d, J = 3.0 Hz), 6.9 (1H, t, J = 7.6 Hz), 7.1-7.3 (4H, m), 7.35-7.45 (1H, m). |
| Reference Example 6 | 7-hydroxy-1-benzyl-1H-indole | 4.91 (1H, brs), 5.65 (2H, s), 6.45-6.55 (2H, m), 6.9 (1H, t, J = 7.7 Hz), 7.0-7.35 (7H, m). |

Example 1

7-(1-β-Glucopyranosyloxy)-1-(4-methylbenzyl)-1H-indole

[Chem. 6]

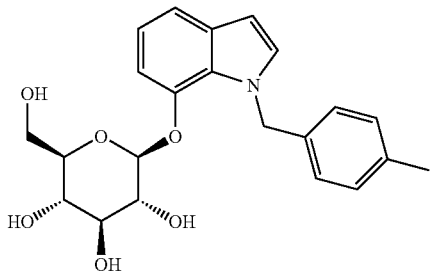

To a mixture of 7-hydroxy-1-(4-methylbenzyl)-1H-indole (1.36 g), acetobromo-α-D-glucose (2.59 g) and benzyltri-(n-butyl)ammonium chloride (1.79 g) in methylene chloride (20 mL) was added 5 mol/L aqueous sodium hydroxide solution (3.4 mL), and the mixture was stirred at room temperature overnight. The reaction mixture was purified by column chromatography on aminopropylated silica gel (eluent: n-hexane/ethyl acetate 1/1), and purified by column chromatography on silica gel (eluent: n-hexane/ethyl acetate=3/1-2/1) to give 7-(2,3,4,6-tetra-O-acetyl-β-D-glucopyranosyloxy)-1-(4-methylbenzyl)-1H-indole (1.25 g). The obtained 7-(2,3,4,6-tetra-O-acetyl-β-D-glucopyranosyloxy)-1-(4-methylbenzyl)-1H-indole (0.3 g) was dissolved in methanol (2 mL). To the solution was added sodium methoxide (28% methanol solution, 0.05 mL), and the mixture was stirred at room temperature for 1 hour. The reaction mixture was purified by column chromatography on silica gel (eluent: methylene chloride/methanol=5/1) to give the title compound (0.19 g).

¹H-NMR (CD₃OD) δ ppm:
2.26 (3H, s), 3.3-3.5 (4H, m), 3.66 (1H, dd, J=11.9 Hz, 5.6 Hz), 3.86 (1H, dd, J=11.9 Hz, 2.2 Hz), 5.05 (1H, d, J=7.8 Hz), 5.49 (1H, d, J=15.6 Hz), 5.89 (1H, d, J=15.6 Hz), 6.42 (1H, d, J=3.1 Hz), 6.85-6.95 (2H, m), 6.95-7.15 (5H, m), 7.15-7.25 (1H, m).

Examples 2 to 5

The compounds described in Table 2 were prepared in a similar manner to that described in Example 1 using the corresponding starting materials.

TABLE 2

| No. | Structure Formula | ¹H-NMR (CD₃OD) δ ppm: |
|---|---|---|
| Example 2 | 7-(β-D-glucopyranosyloxy)-1-(4-methoxybenzyl)-1H-indole derivative | 3.3-3.55 (4H, m), 3.67 (1H, dd, J = 12.0 Hz, 5.8 Hz), 3.73 (3H, s), 3.87 (1H, dd, J = 12.0 Hz, 2.2 Hz), 5.07 (1H, d, J = 7.5 Hz), 5.47 (1H, d, J = 15.6 Hz), 5.86 (1H, d, J = 15.6 Hz), 6.4 (1H, d, J = 2.8 Hz), 6.75-6.85 (2H, m), 6.85-6.95 (2H, m), 7.05-7.15 (3H, m), 7.15-7.25 (1H, m). |

TABLE 2-continued

| No. | Structure Formula | $^1$H-NMR (CD$_3$OD) δ ppm: |
|---|---|---|
| Example 3 | | 1.9-2.0 (2H, m), 3.3-3.55 (4H, m), 3.65-3.75 (3H, m), 3.87 (1H, dd, J = 11.9 Hz, 2.2 Hz), 4.01 (2H, t, J = 6.4 Hz), 5.07 (1H, d, J = 7.5 Hz), 5.46 (1H, d, J = 15.4 Hz), 5.86 (1H, d, J = 15.4 Hz), 6.4 (1H, d, J = 3.1 Hz), 6.75-6.85 (2H, m), 6.85-6.95 (2H, m), 7.05-7.15 (3H, m), 7.15-7.25 (1H, m). |
| Example 4 | | 3.05-3.2 (2H, m), 3.4-3.55 (3H, m), 3.55-3.65 (1H, m), 3.71 (1H, dd, J = 12.2 Hz, 5.4 Hz), 3.91 (1H, dd, J = 12.2 Hz, 2.2 Hz), 4.45-4.55 (1H, m), 4.8-4.9 (1H, m), 5.19 (1H, d, J = 8.0 Hz), 6.25 (1H, d, J = 3.0 Hz), 6.81 (1H, d, J = 3.0 Hz), 6.9-7.0 (2H, m), 7.1-7.25 (6H, m). |
| Example 5 | | 3.3-3.5 (4H, m), 3.66 (1H, dd, J = 11.8 Hz, 5.6 Hz), 3.86 (1H, dd, J = 11.8 Hz, 2.2 Hz), 5.05 (1H, d, J = 7.3 Hz), 5.54 (1H, d, J = 15.8 Hz), 5.96 (1H, d, J = 15.8 Hz), 6.43 (1H, d, J = 3.2 Hz), 6.85-6.95 (2H, m), 7.1-7.3 (7H, m). |

Example 6

1-[2-(4-Hydroxyphenyl)ethyl]-7-(2,3,4,6-tetra-O-pivaloyl-β-D-glucopyranosyloxy)-1H-indole

[Chem. 7]

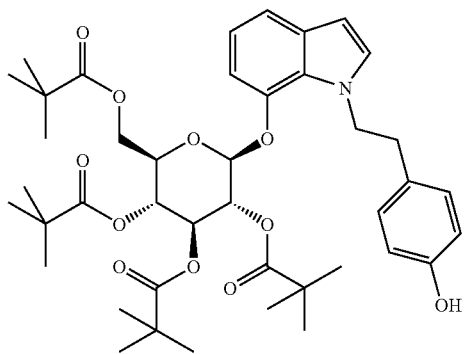

To a mixture of 7-hydroxy-1-{2-[4-(3,3-dimethoxy-propoxy)phenyl]ethyl}-1H-indole (1.57 g), 2,3,4,6-tetra-O-pivaloyl-α-D-glucopyranosyl bromide (2.56 g) and benzyltri-(n-butyl)ammonium chloride (1.38 g) in methylene chloride (15 mL) was added 5 mol/L aqueous sodium hydroxide solution (2.7 mL), and the mixture was stirred at room temperature for 2 days. The reaction mixture was purified by column chromatography on aminopropylated silica gel (eluent: n-hexane/ethyl acetate=1/1), and purified by column chromatography on silica gel (eluent: n-hexane/ethyl acetate=6/1-4/1) to give 1-{2-[4-(3,3-dimethoxypropoxy)phenyl]ethyl}-7-(2,3,4,6-tetra-O-pivaloyl-β-D-glucopyranosyloxy)-1H-indole (1.05 g). This material was dissolved in acetone (12 mL). To the solution were added water (6 mL) and oxalic acid dihydrate, and the mixture was heated for reflux for 2 hours. To the reaction mixture was added piperazine (0.64 g), and the mixture was stirred at room temperature for 3 hours. The reaction mixture was poured into water, and the resulting mixture was extracted with ethyl acetate. The ethyl acetate solution was washed with water and brine, and dried over anhydrous magnesium sulfate. The solvent was removed under reduced pressure, and the residue was purified by column chromatography on silica gel (eluent: n-hexane/ethyl acetate=4/1), and purified by column chromatography on aminopropylated silica gel (n-hexane/ethyl acetate=4/1-3/1-2/1) to give the title compound (0.31 g).

$^1$H-NMR (CDCl$_3$) δ ppm:
1.1 (9H, s), 1.12 (9H, s), 1.16 (9H, s), 1.18 (9H, s), 2.9-3.05 (2H, m), 3.85-3.95 (1H, m), 4.05-4.2 (2H, m), 4.25-4.4 (1H, m), 4.5-4.65 (1H, m), 4.7 (1H, s), 5.15-5.25 (1H, m), 5.4-5.55 (3H, m), 6.29 (1H, d, J=2.9 Hz), 6.64 (1H, d, J=2.9 Hz), 6.65-6.7 (2H, m), 6.71 (1H, d, J=7.7 Hz), 6.8-6.85 (2H, m), 6.93 (1H, t, J=7.7 Hz), 7.25-7.3 (1H, m).

Example 7

7-(β-D-Glucopyranosyloxy)-1-[2-(4-hydroxyphenyl)ethyl]-1H-indole

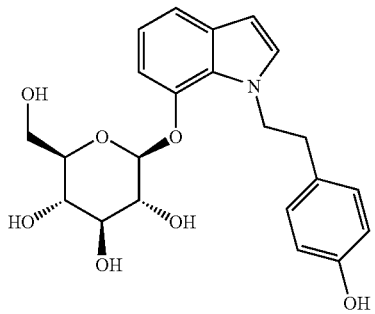

[Chem. 8]

To a solution of 1-[2-(4-hydroxyphenyl)ethyl]-7-(2,3,4,6-tetra-O-pivaloyl-β-D-glucopyranosyloxy)-1H-indole (50 mg) in methanol (1 mL) were added water (0.1 mL) and lithium hydroxide monohydrate (11 mg), and the mixture was stirred at room temperature overnight. The reaction mixture was purified by column chromatography on silica gel (eluent: methylene chloride/methanol=8/1-5/1) to give the title compound (20 mg).

$^1$H-NMR (CD$_3$OD) δ ppm:
2.9-3.1 (2H, m), 3.4-3.55 (3H, m), 3.55-3.65 (1H, m), 3.71 (1H, dd, J=12.1 Hz, 5.3 Hz), 3.91 (1H, dd, J=12.1 Hz, 2.0 Hz), 4.35-4.5 (1H, m), 4.75-4.9 (1H, m), 5.18 (1H, d, J=7.8 Hz), 6.26 (1H, d, J=3.2 Hz), 6.6-6.7 (2H, m), 6.83 (1H, d, J=3.2 Hz), 6.85-6.95 (4H, m), 7.15-7.2 (1H, m).

Example 8

7-(β-D-Glucopyranosyloxy)-1-[2-(4-methoxyphenyl)ethyl]-1H-indole

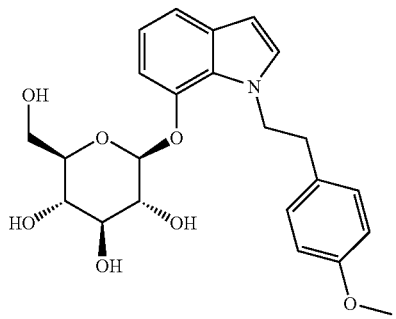

[Chem. 9]

A mixture of 1-[2-(4-hydroxyphenyl)ethyl]-7-(2,3,4,6-tetra-O-pivaloyl-β-D-glucopyranosyloxy)-1H-indole (50 mg), cesium carbonate (43 mg) and methyl iodide (0.008 mL) in acetone (2 mL) was stirred at room temperature overnight. The reaction mixture was purified by column chromatography on aminopropylated silica gel (eluent: n-hexane/ethyl acetate=5/1) to give 1-[2-(4-methoxyphenyl)ethyl]-7-(2,3,4,6-tetra-O-pivaloyl-β-D-glucopyranosyloxy)-1H-indole (51 mg). This material was dissolved in methanol (1 mL). To the solution were added water (0.1 mL) and lithium hydroxide monohydrate (13 mg), and the mixture was stirred at room temperature overnight. The reaction mixture was purified by column chromatography on silica gel (eluent: methylene chloride/methanol=8/1) to give the title compound (19 mg).

$^1$H-NMR (CD$_3$OD) δ ppm:
2.95-3.15 (2H, m), 3.35-3.55 (3H, m), 3.55-3.65 (1H, m), 3.65-3.8 (4H, m), 3.91 (1H, dd, J=11.9 Hz, 2.3 Hz), 4.35-4.5 (1H, m), 4.75-4.9 (1H, m), 5.19 (1H, d, J=8.1 Hz), 6.25 (1H, d, J=3.0 Hz), 6.7-6.85 (3H, m), 6.85-7.05 (4H, m), 7.1-7.2 (1H, m).

Example 9

7-(β-D-Glucopyranosyloxy)-1-[2-(4-{3-[2-hydroxy-1,1-bis-(hydroxymethyl)ethylamino]propoxy}phenyl)ethyl]-1H-indole

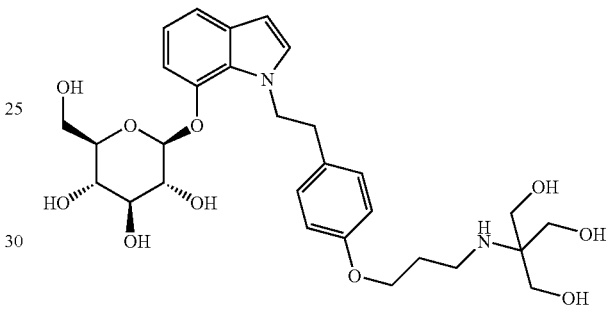

[Chem. 10]

A mixture of 1-[2-(4-hydroxyphenyl)ethyl]-7-(2,3,4,6-tetra-O-pivaloyl-β-D-glucopyranosyloxy)-1H-indole (0.2 g), cesium carbonate (0.17 g) and 1-bromo-3-chloropropane (0.05 mL) in acetone (4 mL) was stirred at room temperature overnight. The reaction mixture was purified by column chromatography on silica gel (eluent: n-hexane/ethyl acetate=6/1) to give 1-{2-[4-(3-chloropropoxy)phenyl]ethyl}-7-(2,3,4,6-tetra-O-pivaloyl-β-D-glucopyranosyloxy)-1H-indole (0.21 g). This material was dissolved in acetonitrile (6 mL). To the solution was added sodium iodide (46 mg), and the mixture was heated for reflux overnight. To the reaction mixture were added tris(hydroxymethyl)aminomethane (0.31 g) and ethanol (4 mL), and the mixture was stirred at 60° C. for 2 days. The reaction mixture was purified by column chromatography on aminopropylated silica gel (eluent: methylene chloride/methanol=30/1-5/1) to give 1-[2-(4-{3-[2-hydroxy-1,1-bis(hydroxymethyl)ethyl-amino]propoxy}phenyl)ethyl]-7-(2,3,4,6-tetra-O-pivaloyl-β-D-glucopyranosyloxy)-1H-indole (0.13 g). This material was dissolved in methanol (3 mL). To the solution were added water (0.3 mL) and lithium hydroxide monohydrate (24 mg), and the mixture was stirred at room temperature overnight. The reaction mixture was concentrated under reduced pressure, and the residue was purified by solid phase extraction method on ODS (washing solvent: distilled water, eluent: methanol) to give the title compound (71 mg).

$^1$H-NMR (CD$_3$OD) δ ppm:
1.85-2.0 (2H, m), 2.81 (2H, t, J=7.0 Hz), 2.95-3.15 (2H, m), 3.35-3.65 (10H, m), 3.71 (1H, dd, J=11.9 Hz, 5.3 Hz), 3.9 (1H, dd, J=11.9 Hz, 2.3 Hz), 4.02 (2H, t, J=6.2 Hz), 4.4-4.5 (1H, m), 4.75-4.9 (1H, m), 5.18 (1H, d, J=7.8 Hz), 6.25 (1H, d, J=3.2 Hz), 6.75-6.85 (3H, m), 6.85-6.95 (2H, m), 6.95-7.05 (2H, m), 7.1-7.2 (1H, m).

Example 10

7-(β-D-Glucopyranosyloxy)-1-(4-methylbenzyl)-1H-benzimidazole

[Chem. 11]

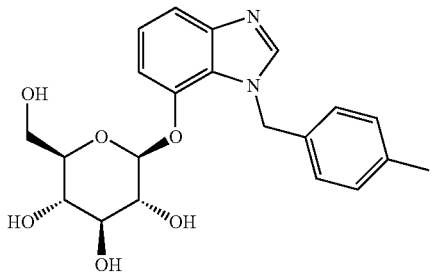

To a mixture of 2-amino-3-nitrophenol (0.5 g), 2,3,4,6-tetra-O-pivaloyl-α-D-glucopyranosyl bromide (1.88 g) and benzyltri(n-butyl)ammonium chloride (1.01 g) in methylene chloride (15 mL) was added 5 mol/L aqueous sodium hydroxide solution (3.24 mL), and the mixture was stirred at room temperature for 4 days. The reaction mixture was poured into 0.5 mol/L hydrochloric acid, and the resulting mixture was extracted with ethyl acetate. The extract was washed with 0.5 mol/L hydrochloric acid, water and brine, and dried over anhydrous magnesium sulfate. The solvent was removed under reduced pressure, and the residue was purified by column chromatography on silica gel (eluent: n-hexane/ethyl acetate=4/1) to give 2-amino-3-nitrophenyl 2,3,4,6-tetra-O-pivaloyl-β-D-glucopyranoside (0.99 g). This material was dissolved in tetrahydrofuran (15 mL). To the solution was added 10% palladium-carbon powder (500 mg), and the mixture was stirred at room temperature under a hydrogen atmosphere overnight. The insoluble material was removed by filtration, and the filtrate was concentrated under reduced pressure. The residue was purified by column chromatography on silica gel (eluent: n-hexane/ethyl acetate=3/1-1.5/1) to give 2,3-diaminophenyl 2,3,4,6-tetra-O-pivaloyl-β-D-glucopyranoside (0.53 g). To the obtained 2,3-diaminophenyl 2,3,4,6-tetra-O-pivaloyl-β-D-glucopyranoside (0.2 g) were added triethyl orthoformate (0.24 g) and a catalytic amount of p-toluenesulfonic acid monohydrate, and the mixture was stirred at 130° C. for 3 minutes. The reaction mixture was purified by column chromatography on silica gel (eluent: n-hexane/ethyl acetate=1/1-1/2) to give 4-(2,3,4,6-tetra-O-pivaloyl-β-D-glucopyranosyloxy)-1H-benzimidazole (0.16 g). To this material were added cesium carbonate (0.13 g), 4-methylbenzyl chloride (40 mg), a catalytic amount of sodium iodide and N,N-dimethylformamide (4 mL), and the mixture was stirred at room temperature overnight. The reaction mixture was poured into water, and the precipitated crystals were collected by filtration. The crystals were washed with water and dried under reduced pressure to give a mixture (0.16 g) of 1-(4-methylbenzyl)-7-(2,3,4,6-tetra-O-pivaloyl-β-D-glucopyranosyloxy)-1H-benzimidazole and 1-(4-methylbenzyl)-4-(2,3,4,6-tetra-O-pivaloyl-β-D-glucopyranosyloxy)-1H-benzimidazole. This material was dissolved in methanol (2 mL). To the solution were added water (0.2 mL) and lithium hydroxide monohydrate (43 mg), and the mixture was stirred at room temperature for 8 hours. After purification of the reaction mixture by column chromatography on silica gel (eluent: methylene chloride/methanol=5/1), the crystals obtained by concentration of the fractions were treated with methanol. The precipitated isomer was removed by filtration, and the filtrate was concentrated under reduced pressure to give the title compound (12 mg).

$^1$H-NMR (CD$_3$OD) δ ppm:
2.29 (3H, s), 3.3-3.55 (4H, m), 3.68 (1H, dd, J=12.4 Hz, 6.2 Hz), 3.88 (1H, dd, J=12.4 Hz, 2.2 Hz), 5.08 (1H, d, J=7.5 Hz), 5.61 (1H, d, J=15.3 Hz), 5.86 (1H, d, J=15.3 Hz), 7.05-7.2 (6H, m), 7.33 (1H, d, J=8.0 Hz), 8.09 (1H, s).

Test Example 1

Assay for Inhibitory Effects on Human SGLT Activity

1) Cloning and Construction of the Vector Expressing Human SGLT1

The cDNA library was prepared for PCR amplification by reverse transcription from total RNA derived from human small intestine (Ori gene) using oligo-dT as a primer. Using this cDNA library as a template, the DNA fragment coding 1 to 2005 bp of human SGLT1 (ACCESSION: M24847), which was reported by Hediger et al., was amplified by PCR method and inserted into the multi-cloning site of pcDNA3.1(−) (Invitrogen). The DNA sequence inserted was perfectly matched to the previously reported sequence.

2) Cloning and Construction of the Vector Expressing Human SGLT2

The cDNA library was prepared for PCR amplification by reverse transcription from total RNA derived from human kidney (Ori gene) using oligo-dT as a primer. Using this cDNA library as a template, the DNA fragment coding 2 to 2039 bp of human SGLT2 (ACCESSION: M95549, M95299), which was reported by R. G. Wells et al., was amplified by PCR method and inserted into the multi-cloning site of pcDNA3.1(−) (Invitrogen). The DNA sequence inserted was perfectly matched to the previously reported sequence.

3) Preparation of the Cells Expressing Human SGLT1 or SGLT2

The vector expressing human SGLT1 or SGLT2 was transfected into COS-7 cells by lipofection method (Lipofectamine-2000: Invitrogen). First, COS-7 cells were plated 5×10$^4$ cells/100 μL/well on 96-wells plate and incubated at 37° C. for 2 hours. In addition, per 50 μL medium, 0.3 μg of human SGLT1 or SGLT2 expression vector was mixed with 0.5 μL of Lipofectamine-2000 and the complex solution was prepared. Fifty μL/well of this complex solution was added to COS-7 cells, previously described, and the plate was mixed gently and was used for uptake assay after 2 days culture.

4) Measurement of the Inhibitory Activity Against the Uptake of Methyl-α-D-glucopyranoside (α-MG)

A mixture of non-labeled (Sigma) and $^{14}$C-labeled α-MG (Amersham Pharmacia Biotech) was added to the uptake buffer (pH 7.4; containing 140 mM sodium chloride, 2 mM potassium chloride, 11 mM calcium chloride, 1 mM magnesium chloride, 10 mM 2-[4-(2-hydroxyethyl)-1-piperazinyl] ethane sulfonic acid and 5 mM tris(hydroxymethyl)aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal uptake measurement buffer, which contains 140 mM choline chloride instead of sodium chloride, was prepared. After removing the culture medium of cells expressing human SGLT1 or human SGLT2, 180 μL of the pre-treatment buffer (the basal uptake buffer without α-MG) was added to each well and incubated at 37° C. for 10 minutes. After repeating the same treatment, the pre-treatment buffer was removed, and then 75 μL per well of the measurement buffer or the basal uptake buffer was added and the cells were incubated at 37° C. After 1 hour incubation, the measurement buffer was removed and the cells were washed twice with 180 μL per well of the washing buffer (the basal uptake buffer containing 10 mM non-labeled α-MG). The cells were solubilized by 75 μL per well of 0.2 mol/L sodium hydroxide, and then the cell lysates were transferred into PicoPlates (Packard). One hundred fifty μL of Microscint-40 (Packard) was added to the wells and mixed. Radioactivity was measured by means of micro-scintillation counter TopCount (Packard). One hundred % was set to the difference between the uptake in the control group and the basal uptake, and the uptake of methyl α-D-glucopyranoside at each drug concentration was calculated. The drug concentration, at which 50% uptake of methyl α-D-glucopyranoside was inhibited ($IC_{50}$ value), was calculated using logit plot. The results are shown in Table 3.

TABLE 3

| Test compound | human SGLT1 $IC_{50}$ (nM) | Test compound | human SGLT2 $IC_{50}$ (nM) |
|---|---|---|---|
| Example 1 | 235 | Example 4 | 66 |
| Example 7 | 52 | Example 7 | 16 |

As shown in Table 3, 1-substituted-7-(β-D-glycopyranosyloxy)(aza)indole compounds (I) of the present invention have an extremely potent inhibitory activity against a human SGLT1 and/or human SGLT2.

INDUSTRIAL APPLICABILITY

The 1-substituted-7-(β-D-glycopyranosyloxy)(aza)-indole compound (I) of the present invention or a prodrug thereof, or a pharmaceutically acceptable salt thereof, or a hydrate or solvate thereof has an SGLT inhibitory activity against human SGLT, and therefore, can suppress postprandial increase of blood glucose and/or normalize blood glucose by inhibiting absorption of carbohydrates such as glucose at the small intestine or by inhibiting reabsorption of glucose at the kidney. Therefore, the present invention can provide agents for the prevention or treatment of diabetes, postprandial hyperglycemia, impaired glucose tolerance, diabetic complications, obesity or the like.

The invention claimed is:

1. A 1-substituted-7-(β-D-glycopyranosyloxy)(aza) indole compound represented by the following general formula (I), or a pharmaceutically acceptable salt thereof:

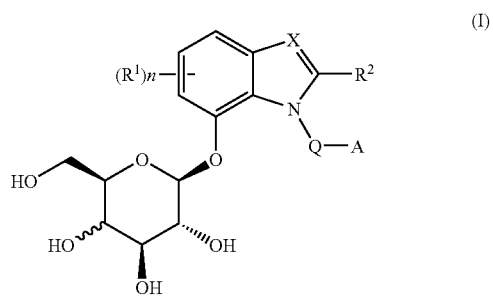

wherein $R^1$ represents a halogen atom, an alkyl group, a hydroxyalkyl group, an alkoxyalkyl group, a hydroxy group, an alkoxy group, a cycloalkyloxy group, an amino group, a (di)alkylamino group, a carboxyl group or a cyano group;

n represents an integer number from 0 to 3;

$R^2$ represents a hydrogen atom, a halogen atom, an alkyl group, a hydroxyalkyl group, an alkoxyalkyl group, a hydroxy group, an alkoxy group, a cycloalkyloxy group, an amino group, a (di)alkylamino group, a carboxyl group or a cyano group;

X represents a carbon atom which a hydrogen atom or a group selected from a group consisting of a halogen atom, an alkyl group, a hydroxyalkyl group, an alkoxyalkyl group, a hydroxy group, an alkoxy group, a cycloalkyloxy group, an amino group, a (di)alkylamino group, a carboxyl group and a cyano group binds to;

Q represents an alkylene group; and

A represents an aryl group or a heteroaryl group each of which may have a substituent selected from the group consisting of a halogen atom, a hydroxy group and a cyano group; an alkyl group, an alkenyl group, an alkynyl group, an alkoxy group, an alkylthio group, an alkylsulfinyl group and an alkylsulfonyl group, each of which may have a substituent α; a (hetero)aryl group and a (hetero)cycloalkyl group, each of which may have a substituent α and optionally bind to a (hetero)aryl group via an alkylene group, —O—, —NH— or —S—: a —U—V—W—N($R^A$)—Y—Z group, and a —U—V—COO—Y—$R^B$ group, wherein:

U means a single bond, —O— or —S—,

V means a single bond, or an alkylene group or an alkenylene group, each of which may have a hydroxy group, W means a single bond, —CO—, —$SO_2$— or —C(=NH)—, $R^A$ means a hydrogen atom, or an alkyl group, a (hetero)aryl group or a (hetero)cycloalkyl group, each of which may have a substituent α, Y means a single bond or an alkylene group which may have an oxo group, Z means a hydrogen atom; a formyl group; or an alkyl group, a (hetero)aryl group or a (hetero)cycloalkyl group, each of which may have a substituent α; an acyl group which may have a substituent α; an alkoxy group or an arylalkoxycarbonyl group, each of which may have a substituent α; —CON($R^K$)($R^L$), —CSN($R^K$)($R^L$), —$SO_2$N($R^K$)($R^L$) or —C(=N$R^K$)N($R^L$)($R^M$); one to three amino acid residues wherein the terminal carboxyl group is an alkoxycarbonyl group optionally having a hydroxy group, an alkoxy group, an amino group or a (di)alkylamino group; an amide with an alicyclic amine or an alkylamine, each of which may have an alkyl group, a (hetero)cycloalkyl group, an alkoxycarbonyl group or an acyl group, each of which may have a hydroxy group, an alkoxy group, an amino group or a (di)alkylamino group; or a carboxamide group; or an aliphatic, a (hetero)cycloalkyl or a (hetero)aryl carboxylic acid residue having an alicyclic amine, which may have an alkyl group, a (hetero)cycloalkyl group, an alkoxycarbonyl group or an acyl group, each of which may have a hydroxy group, an alkoxy group, an amino group or a (di)alkylamino group, in which $R^K$, $R^L$ and $R^M$ independently mean a hydrogen atom, a nitro group, a cyano group, a sulfamoyl group, an acyl group, an alkoxycarbonyl group, an aryl group, an alkylsulfonyl group or an alkyl group optionally having a substituent α, $R^A$ and a part of a group forming Z, each of which binds to a nitrogen atom, may bind together to form an alicyclic amine optionally having a substituent α, $R^B$ means a hydrogen atom; an alkoxyalkyl group having a carboxyl group or an alkoxycarbonyl group; an alkyl group, a (hetero)aryl group or a (hetero)cycloalkyl group, each of which may have a substituent α; one to three amino acid residues wherein the terminal carboxyl group may be an alkoxycarbonyl group optionally having a hydroxy group, an alkoxy group, an amino group or a (di)alkylamino group; an amide with an alicyclic amine or an alkylamine, each of which may have an alkyl group, a (hetero)cycloalkyl group, an alkoxycarbonyl group or an acyl group, each of which may have a hydroxy group, an alkoxy group, an amino group or a (di)alkylamino group; or a carbamoyl group; or an aliphatic, a (hetero)cycloalkyl or a (hetero)aryl carboxylic acid residue having an alicyclic amine, which may have an alkyl group, a (hetero)cycloalkyl group, an alkoxycarbonyl group or an acyl group, each of which may have a hydroxy group, an alkoxy group, an amino group or a (di)alkylamino group, substituent α means a group selected from a group consisting of a halogen atom, an alkyl group, a hydroxyalkyl group, an alkoxyalkyl group, a hydroxy group, an alkoxy group, an amino group, a (di)alkylamino group, a cyano group, a carboxyl group, a carbamoyl group, an alkoxycarbonyl group, a hydroxyalkoxycarbonyl group, a (hetero)aryl group and a (hetero)cycloalkyl group, provided that when U is —O— or —S—, V and W are not a single bond at the same time.

2. A 1-substituted-7-((3-D-glycopyranosyloxy)(aza)indole compound as claimed in claim 1, wherein X represents a carbon atom which a hydrogen atom binds to, or a pharmaceutically acceptable salt thereof.

3. An SGLT inhibitor which comprises a 1-substituted-7 (β-D-glycopyranosyloxy)(aza)indole compound as claimed in claim 1, or a pharmaceutically acceptable salt thereof.

4. A pharmaceutical composition which comprises a 1-substituted-7-(β-D-glycopyranosyloxy)(aza)indole compound as claimed in claim 1, or a pharmaceutically acceptable salt thereof.

5. A pharmaceutical composition as claimed in claim 4, which is a glucose or galactose absorption inhibitor.

6. A pharmaceutical composition as claimed in claim 4, which is a glucose reabsorption inhibitor.

7. A pharmaceutical composition as claimed in claim 4, which is an agent for the treatment of a disease selected from a group consisting of postprandial hyperglycemia, diabetes, impaired glucose tolerance, diabetic complications, obesity, hyperinsulinemia, hyperlipidemia, hypercholesterolemia, galactosemia, hypertriglyceridemia, lipid metabolism disorder, atherosclerosis, hypertension, metabolic syndrome, congestive heart failure, edema, hyperuricemia and gout.

8. A combination of a pharmaceutical composition as claimed in claim 4 and at least one drug selected from a group consisting of an insulin sensitivity enhancer, an amylase inhibitor, an α-glucosidase inhibitor, a biguanide, an insulin secretion enhancer, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, an 11β-hydroxysteroiddehydrogenaze inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, an antidiarrhoics, a cathartics, a hydroxymethylglutaryl coenzyme A reductase inhibitor, a fibrate, a $β_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a squalene epoxidase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

* * * * *